US008640558B2

(12) United States Patent
Cabuz

(10) Patent No.: US 8,640,558 B2
(45) Date of Patent: Feb. 4, 2014

(54) SYSTEM FOR THE AUTOMATED INSPECTION OF STRUCTURES AT HEIGHT

(75) Inventor: Cleopatra Cabuz, Eden Prairie, MN (US)

(73) Assignee: Honeywell International Inc., Morristown, NJ (US)

( * ) Notice: Subject to any disclaimer, the term of this patent is extended or adjusted under 35 U.S.C. 154(b) by 197 days.

(21) Appl. No.: 13/230,552

(22) Filed: Sep. 12, 2011

(65) Prior Publication Data
US 2013/0061696 A1 Mar. 14, 2013

(51) Int. Cl.
G01N 21/88 (2006.01)
G01N 29/265 (2006.01)

(52) U.S. Cl.
CPC .................... G01N 29/265 (2013.01)
USPC .......................................................... 73/865.8

(58) Field of Classification Search
USPC ............................................................ 73/865.8
See application file for complete search history.

(56) References Cited

U.S. PATENT DOCUMENTS

| | | | | |
|---|---|---|---|---|
| 3,814,211 A | * | 6/1974 | Pamer | 182/14 |
| 3,911,733 A | * | 10/1975 | Bhuta et al. | 73/800 |
| 4,637,494 A | * | 1/1987 | Iida et al. | 104/288 |
| 4,664,212 A | * | 5/1987 | Nagatsuka et al. | 180/164 |
| 4,688,289 A | * | 8/1987 | Urakami | 15/98 |
| 4,971,591 A | * | 11/1990 | Raviv et al. | 446/177 |
| 4,997,052 A | * | 3/1991 | Urakami | 180/164 |
| 5,193,405 A | * | 3/1993 | Oomichi et al. | 73/865.8 |
| 5,213,172 A | * | 5/1993 | Paris | 180/8.1 |
| 5,318,254 A | * | 6/1994 | Shaw et al. | 244/134 C |
| 5,355,807 A | * | 10/1994 | Pelrine et al. | 105/78 |
| 5,503,033 A | * | 4/1996 | Van Niekerk | 73/865.8 |
| 5,536,199 A | * | 7/1996 | Urakami | 451/91 |
| 5,574,233 A | * | 11/1996 | Oliver et al. | 73/865.8 |
| 5,575,346 A | * | 11/1996 | Yberle | 180/8.6 |
| 5,592,998 A | * | 1/1997 | Urakami | 180/164 |
| 5,609,216 A | * | 3/1997 | Fisher et al. | 180/24.03 |
| 5,633,707 A | * | 5/1997 | Seemann | 356/35.5 |
| 5,672,044 A | * | 9/1997 | Lemelson | 414/744.3 |
| 5,730,553 A | * | 3/1998 | Miura et al. | 405/191 |
| 5,752,577 A | * | 5/1998 | Urakami | 180/164 |
| 5,809,099 A | * | 9/1998 | Kim et al. | 376/249 |
| 5,819,863 A | * | 10/1998 | Zollinger et al. | 180/6.5 |
| 5,839,532 A | * | 11/1998 | Yoshiji et al. | 180/164 |

(Continued)

FOREIGN PATENT DOCUMENTS

JP   1295574 A   11/1989
JP   2146494 A   6/1990

OTHER PUBLICATIONS

Luk et al.; "Climbing Service Robots for Improving Safety in Building Maintenance Industry"; Bioinspiration and Robotics: Walking and Climbing Robots; pp. 127-146; http://www.i-techonline.com/source/pdfs/445/InTech-Climbing_service_robots_for_improving_safety_in_building_maintenance_industry.pdf, Sep. 2007.

(Continued)

Primary Examiner — David A Rogers
(74) Attorney, Agent, or Firm — Conley Rose, P.C.; Kristin Jordan Harkins

(57) ABSTRACT

A method of inspecting a structure comprises providing an inspection apparatus, engaging the inspection apparatus with an access system coupled to a structure, inspecting the access system using the inspection apparatus, and inspecting a portion of the structure using the inspection apparatus.

20 Claims, 4 Drawing Sheets

(56) References Cited

U.S. PATENT DOCUMENTS

| | | | | |
|---|---|---|---|---|
| 5,857,534 A * | 1/1999 | DeVault et al. | ............... | 180/21 |
| 5,858,111 A * | 1/1999 | Marrero | ............... | 134/6 |
| 5,878,099 A * | 3/1999 | Burrows et al. | ............... | 376/260 |
| 5,890,250 A * | 4/1999 | Lange et al. | ............... | 15/50.3 |
| 5,959,424 A * | 9/1999 | Elkmann et al. | ............... | 318/568.12 |
| 6,000,484 A * | 12/1999 | Zoretich et al. | ............... | 180/7.1 |
| 6,046,565 A * | 4/2000 | Thorne | ............... | 318/587 |
| 6,090,221 A * | 7/2000 | Gan et al. | ............... | 134/21 |
| 6,102,145 A * | 8/2000 | Fisher | ............... | 180/164 |
| 6,105,695 A * | 8/2000 | Bar-Cohen et al. | ............... | 180/8.5 |
| 6,170,109 B1 * | 1/2001 | Jesadanont et al. | ............... | 15/50.3 |
| 6,378,387 B1 * | 4/2002 | Froom | ............... | 73/865.8 |
| 6,477,730 B1 * | 11/2002 | Marrero | ............... | 15/53.1 |
| 6,532,840 B2 * | 3/2003 | Hatley et al. | ............... | 73/866.5 |
| 6,633,150 B1 * | 10/2003 | Wallach et al. | ............... | 318/568.12 |
| 6,637,266 B1 * | 10/2003 | Froom | ............... | 73/583 |
| 6,907,799 B2 * | 6/2005 | Jacobsen et al. | ............... | 73/865.8 |
| 6,959,603 B2 * | 11/2005 | Knight et al. | ............... | 73/623 |
| 6,964,312 B2 * | 11/2005 | Maggio | ............... | 180/164 |
| 7,076,335 B2 * | 7/2006 | Seemann | ............... | 700/248 |
| 7,155,307 B2 * | 12/2006 | Seemann | ............... | 700/245 |
| 7,270,021 B2 * | 9/2007 | Shimamura et al. | ............... | 73/865.8 |
| 7,280,890 B2 * | 10/2007 | Seemann | ............... | 700/245 |
| 7,387,475 B2 * | 6/2008 | Beggs et al. | ............... | 408/76 |
| 7,496,454 B2 * | 2/2009 | Rogers et al. | ............... | 702/35 |
| 7,499,772 B2 * | 3/2009 | Wilcox et al. | ............... | 701/3 |
| 7,520,356 B2 * | 4/2009 | Sadegh et al. | ............... | 180/164 |
| 7,681,468 B2 * | 3/2010 | Verl et al. | ............... | 73/865.8 |
| 7,716,989 B2 * | 5/2010 | Kollgaard | ............... | 73/627 |
| 7,872,850 B2 | 1/2011 | Pelrine et al. | | |
| 8,091,440 B2 * | 1/2012 | Kim | ............... | 73/865.8 |
| 8,171,809 B2 * | 5/2012 | Fritz | ............... | 73/865.8 |
| 8,215,435 B2 * | 7/2012 | Dvorak | ............... | 180/164 |
| 8,369,990 B2 * | 2/2013 | Zesch et al. | ............... | 700/245 |
| 2001/0013434 A1 * | 8/2001 | Hopkins | ............... | 180/7.1 |
| 2002/0036108 A1 * | 3/2002 | Jeswine et al. | ............... | 180/164 |
| 2003/0043964 A1 * | 3/2003 | Sorenson | ............... | 378/58 |
| 2003/0177850 A1 * | 9/2003 | Whittington | ............... | 73/865.8 |
| 2004/0227534 A1 * | 11/2004 | Mueller | ............... | 324/758 |
| 2007/0277629 A1 * | 12/2007 | Bagley et al. | ............... | 73/865.8 |
| 2009/0126493 A1 * | 5/2009 | Moore et al. | ............... | 73/618 |
| 2009/0265193 A1 * | 10/2009 | Collins et al. | ............... | 705/4 |
| 2010/0049367 A1 * | 2/2010 | Yang | ............... | 700/259 |
| 2011/0048853 A1 * | 3/2011 | Brickell | ............... | 182/5 |

OTHER PUBLICATIONS

SRI International: "Wall-Climbing Robots; Electroadhesive Robots for Robust Vertical Mobility"; Performance Specifications; youtube.com/innovationsri; Specification Sheet—1 page; http://www.sri.com/robotics/documents/WCRobots_2pg.pdf, 2011.

Vera et al.; Universidad de Cadiz; "Automatic Inspection Systems for Industrial Chimneys"; pp. 1-9; http://www.lalineavertical.com/upload_files/articulo_CICIND_LISBOA_English_preparado.pdf.

Sheth; "Use of Robotics for Nondestructive Inspection of Steel Highway Bridges and Structures"; Virginia Transportation Research Council, Report No. VTRC 05-CR8; Jan. 2005; pp. 1-16; http://trid.trb.org/view.aspx?id=753515.

Shang et al.; "A Cooperative Climbing Robot for Melt Weld Inspection on Large Structures"; 1 page; http://eproceedings.worldscinet.com/9789812835772/9789812835772_0006.html.

* cited by examiner

SYSTEM FOR THE AUTOMATED INSPECTION OF STRUCTURES AT HEIGHT

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Various structures exist that are subject to periodic inspection routines to ensure that the structures are sound, identify potential maintenance issues, and identify compliance with any applicable codes, regulations, and permits. Traditionally, the inspection would be carried out by a person accessing the structure at height using permanent or temporary access structures. For example, various ladders or rails may provide a more or less permanent access structure while temporary scaffolds, lines, or man-lifts may provide temporary access to the structure at height. The inspection process itself requires that a person inspecting the structure scale the structure to provide a visual inspection, thereby placing the inspector in danger if the structure is unsound.

SUMMARY

In an embodiment, a method of inspecting a structure comprises providing an inspection apparatus, engaging the inspection apparatus with an access system coupled to a structure, inspecting the access system using the inspection apparatus, and inspecting a portion of the structure using the inspection apparatus.

In an embodiment, a method of inspecting a structure comprises providing an inspection apparatus comprising a motor; a drive mechanism coupled to an access system, wherein the access system is coupled to a structure; a plurality of sensors; and a power source coupled to the motor and the plurality of sensors; inspecting the access system using a first sensor of the plurality of sensors as the inspection apparatus ascends the access system; inspecting a portion of the structure using a second sensor of the plurality of sensors; and displaying a first output from the first sensor and a second output from the second sensor.

In an embodiment, a method of inspecting a tower structure comprises providing an inspection apparatus configured to engage an access system coupled to a tower structure; engaging the inspection apparatus with the access system; inspecting the access system using a sensor coupled to the inspection apparatus as the inspection apparatus ascends the access system; and inspecting a piece of equipment disposed in an upper portion of the tower structure using the inspection apparatus.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Disclosed herein are methods and systems for providing an unmanned inspection of a structure, including the access system and one or more additional components of a structure. For example, a remote control or automated inspection apparatus may be used to inspect both an access system and a portion of the structure such as a piece of equipment located at the top of the structure. The inspection may be used to detect one or more signs of degradation, wear, fatigue, or other signs of the loss of structural integrity of the access system (e.g., including the connection points connecting the access system to the structure), the structure, and the one or more additional components of the structure. Typical signs may include, but are not limited to, oxidation (e.g., rust, chipped paint, internal voids), failing weld lines, cracks, loose or missing parts, improper connections, failing connections, signs of mechanical wear, and one or more signs of degradation associated with any additional components such as overheating in observable mechanical equipment, fluid leakage, etc. The inspection apparatus may carry one or more sensors to allow the inspection apparatus to detect and record the various signs of degradation, including those not visible to the naked eye.

Information obtained from an inspection using the systems and methods described herein may provide information on the structural integrity of the access system in addition to information on the portion of the structure accessible using the access system. This information could then be used to decide if the access system is safe to climb should a portion of the structure require a further inspection or additional repair and/or maintenance. If the information indicates that the access system needs repair or maintenance, the defects in the access system may be addressed prior to accessing the portion of the structure. Alternatively, should the inspection indicate that the structure falls within acceptable inspection criteria but the access system is damaged, then the access system may be repaired prior to a subsequent inspection of the structure.

Figure 1A:
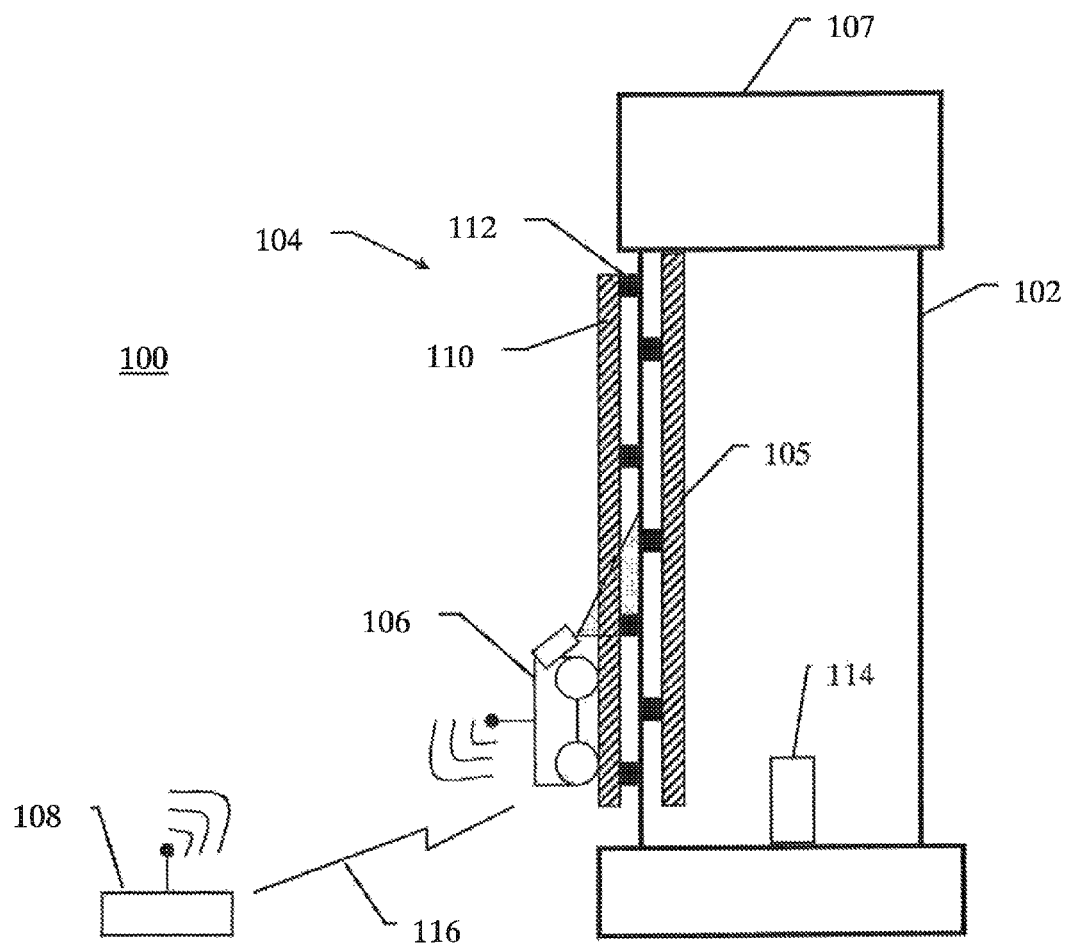
FIGS. 1A and 1B schematically illustrate an inspection system according to an embodiment.
Figure 1B:
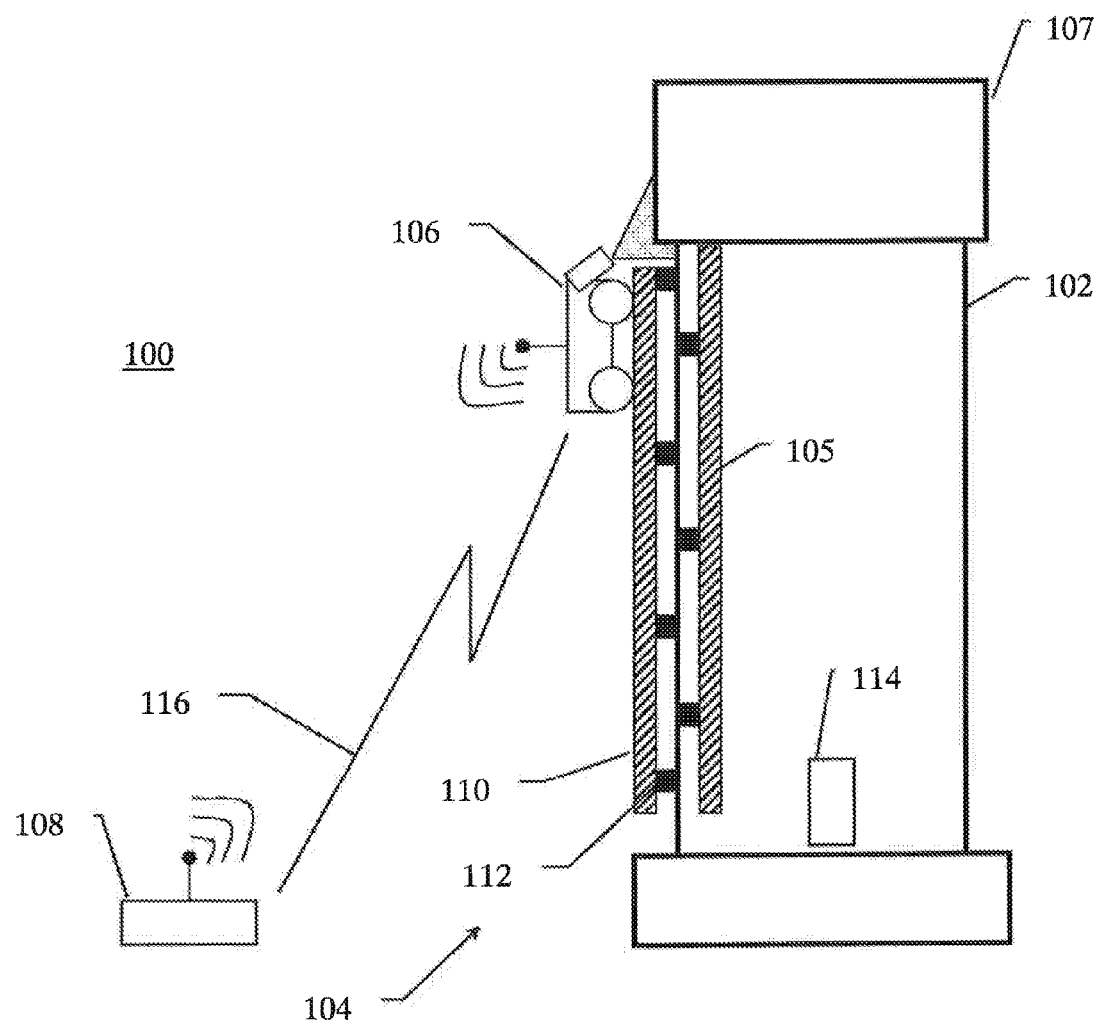

FIG. 1A and FIG. 1B illustrate a system 100 comprising a structure 102, an access system 104 coupled to the structure 102, an upper portion 107, and an inspection apparatus 106 engaging the access system 104. In an embodiment, an optional controller 108 may be in communication with the inspection apparatus 106. As described in more detail herein, the system 100 may be used to inspect the access system and at least a portion of the structure, which may be performed in a single inspection trip.

The structure 102 may comprise any structure that can be inspected and has an access system 104 coupled thereto. For example, suitable structures may include, but are not limited to housing structures, building structures, cell phone towers, wind turbine towers, water tanks, and other suitable structures. The system 100 for inspecting the structure 102 may be used when a simple visual inspection (e.g., by looking at the structure from the ground) is impractical, such as when the structure has a total height (e.g., rooftop height, tower height, etc.) of greater than about 20 ft, greater than about 40 feet, greater than about 60 feet, greater than about 80 feet, or alternatively, greater than about 80 feet. The structure 102 may comprise a plurality of portions including an upper portion 107. The upper portion 107 may include an identifiable structure, element, and/or one or more pieces of equipment located at or near the top of the structure 102. For example, a tank disposed at the top of a water tower may represent the upper portion 107 of the structure. Similarly, a cell phone antenna array located at the top of a cell phone tower, and a wind turbine and associated generator located at the top of a wind turbine tower may represent the upper portion 107 of the corresponding structures. When the structure 102 comprises a building, the upper portion 107 may comprise one or more identifiable components such as rooftop equipment (e.g., elevator equipment, air conditioner equipment, etc.). In an embodiment, the upper portion 107 may comprise about the top 5% of the building height, about the top 10% of the building height, or alternatively, about the top 15% of the building height.

Figure 2:
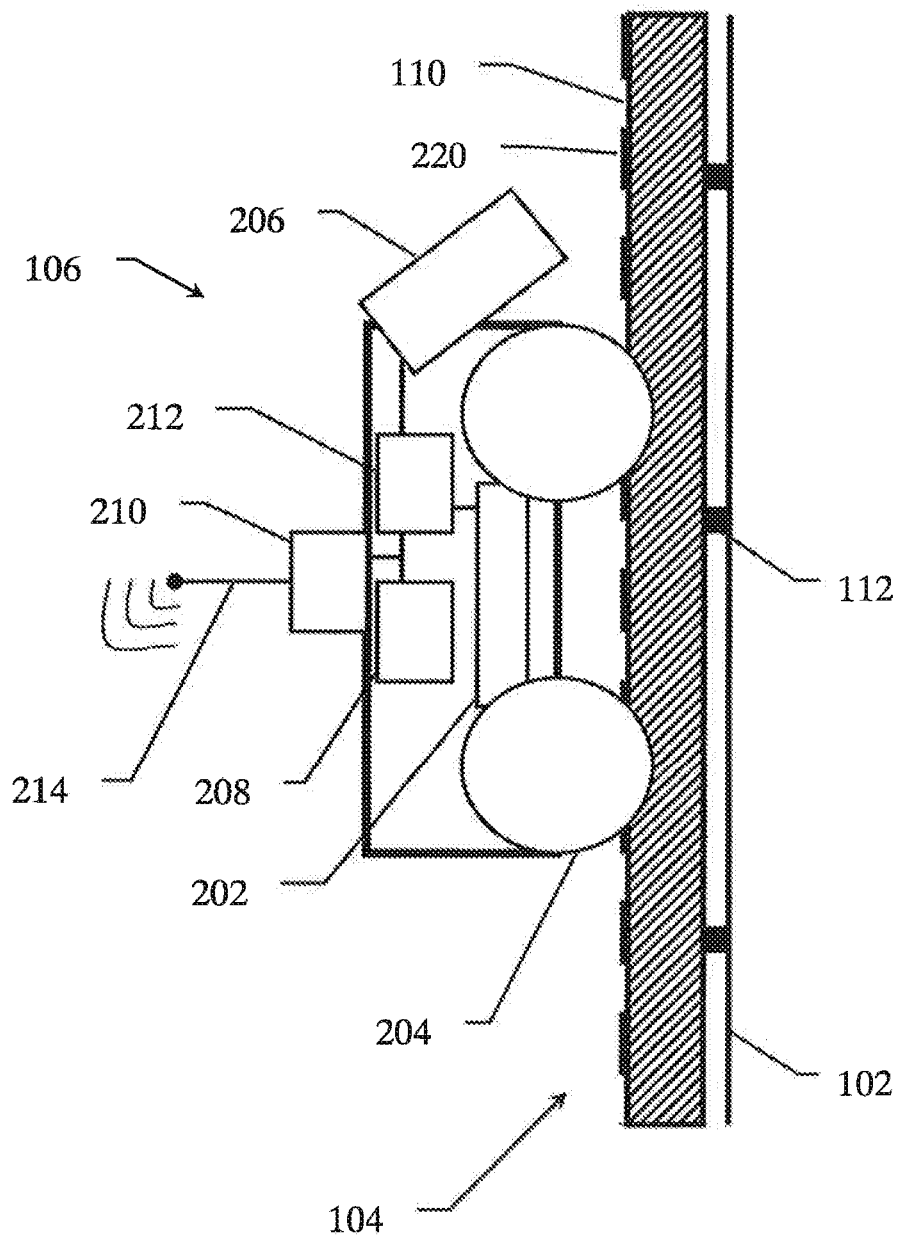
FIG. 2 schematically illustrates an inspection apparatus according to an embodiment.

The access system 104 may be coupled to the structure 102 and may provide a route for the inspection apparatus 106 to traverse the height of the structure 102. The access system 104 may comprise any number of systems, structures, or elements. The access system 104 may comprise various components including the climbing system 110 and one or more connections and/or supporting elements 112 used to couple the climbing system 110 to the structure 102. In an embodiment, the access system 104 may comprise a climbing system 110 suitable for use by a human to access the structure 102. Suitable climbing systems 110 for use by a human may include, but are not limited to, a ladder, a rail, a cable, a stairway, footholds, and the like. The climbing systems 110 may comprise one or more surface features formed during manufacturing, during installation, and/or after installation configured to interact with the inspection apparatus 106. For example, a rail (e.g., a ladder rail, a stairway rail, an elevator rail, etc.) may comprise one or more notches or gear teeth (teeth 220 as shown, for example, in FIG. 2) for engaging a corresponding set of gear teeth or notches on an inspection apparatus 106. In another embodiment, a climbing structure 110 may comprise one or more surface features such as a roughened surface to interact with one or more gripping surfaces of the inspection apparatus 106.

The access system 104 may also comprise suitable connections and/or supporting elements 112 used to couple the climbing system 110 to the structure 102. Suitable connections and/or supporting elements 112 may include, but are not limited to, a bracket, a beam, a cable, and one or more connectors (e.g., a bolt, a screw, an anchor, a welded joint, a clamp, etc.). For example, a stairway may be supported on a cross beam that is coupled to a wall of the structure 102 through the use of a bracket and one or more bolts or concrete anchors. In an embodiment, the access system 104 is configured to be permanently attached to the structure 102. As used herein, the term "permanently attached" is intended to convey that the access system 104 would be coupled to the structure 102 for the useful life of the access system 104 and/or the structure 102. However, the term "permanently attached" does not preclude the possibility that the access system 104 could be removed if needed and/or that degradation of one or more of the components of the access system 104 could result in a de-coupling of a portion of the access system 104 from the structure 102.

The access system 104 may comprise any combination of climbing systems 110 and/or connections/supporting elements 112. For example, some industrial climbing systems may comprise a ladder in combination with a cable. The cable may be present to provide a connection point for a fall protection mechanism. The ladder may be bolted to a structure, and the cable may be clamped to the structure or the ladder at one or more ends and/or at one or more points along the ladder. When a plurality of climbing structures, and/or connections and/or supporting elements 112 are present, the inspection apparatus 106 may use one or more of the available components of the access system 104 to traverse the height of the structure 102.

The access system 104 may be coupled to any portion of the structure 102. For example, the access system 104 may be disposed on or coupled to an outer surface of the structure 102. This configuration may be typical when the interior of the structure 102 is occupied and the access system 104 is used to provide access to an upper portion 107 of the structure 102. The access system 104 may also be coupled to an interior portion of the structure 102. For example, access system 105 is illustrated in FIG. 1A coupled to the interior of the structure 102. One or more access locations 114 may be associated with a structure 102 to allow access to an interior access system 105. Such interior access systems 105 may be used when one or more interior access passageways are present within a structure 102. Such interior access passageways may be present in wind turbine towers, elevator shafts within buildings, water towers, stairwells within buildings, and the like. Structures 102 suitable for use with the systems and methods described herein may comprise a plurality of access systems, including both interior access systems and exterior access systems.

The inspection apparatus 106 may comprise any suitable unmanned device capable of traversing the height of the structure using the access system 104, observing the access system 104, and observing at least a portion of the structure 102. In an embodiment as shown schematically in FIG. 2, the inspection apparatus 106 comprises a motorized device comprising a motor 202, a drive mechanism 204 coupled to the motor 202 and configured to engage the climbing system 110, a sensor 206, and a power source 208 coupled to the motor 202 and the sensor 206. The inspection apparatus 106 may also comprise a communication system 210 for sending and/or receiving signals such as control signals, sensor outputs, status indicators, etc. A memory 212 may optionally be coupled to the inspection apparatus 106 to store one or more control programs and/or sensor outputs. It will be appreciated that one or more components of the inspection apparatus 106 may be light weight components to limit the total weight of the inspection apparatus 106. Lighter components may allow for use of a correspondingly smaller motor 202, drive mechanism 204, and power source 208.

The motor 202 may comprise any suitable motor capable of providing the force necessary to drive the inspection apparatus 106 upwards along the length of the access system 104. The motor 202 and/or a braking system may be used to convey the inspection apparatus 106 downward along the length of the access system 104. Various suitable electrical motors are known and may be appropriately coupled to the drive mechanism 204 through one or more intermediate gears, couplings, and/or connections. The drive mechanism 204 may be configured to engage the access system 104 or any portion thereof (e.g., the climbing system 110, etc.) and traverse along the length of the access system 104. The configuration of the drive mechanism 204 may depend on the type of access system 104, climbing system 110, and/or connections and/or supporting elements 112 used. For example, the configuration of the drive mechanism 204 may vary to allow the inspection apparatus 106 to climb and descend on a ladder, a rail, or on a simple surface such as a cable, each of which may or may not have surface features to interact with the drive mechanism 204. Suitable drive mechanisms 204 for use with the methods and systems described herein may include, but are not limited to, suction cups with or without vacuum assist, pendulum motion devices, cam and crank mechanism, magnetic attraction mechanisms, gear and rail mechanisms, and any other suitable drive mechanisms capable of engaging one or more of the climbing systems 110 described herein, where the climbing systems 110 may or may not comprise surface features for interacting with the drive mechanism 204. Any combination of these drive mechanisms 204 may be used. For example, a magnetic attraction mechanism may be used in combination with a cam and crank mechanism to maintain the engagement of the inspection apparatus 106 with the access system 104 and drive the inspection apparatus 106 upwards along the length of the access system 104.

The inspection apparatus 106 comprises at least one sensor 206 to observe the access system 104 and/or the structure 102 (e.g., the upper portion 107 of the structure 102). Various suitable sensors 206 may be used and may be chosen based on the type of structure 102 being inspected, the type of access system 104 being traversed by the inspection system 106, the type of equipment and/or structures in the upper portion 107 of the structure 102, and/or the type of degradation expected or being sought out. Suitable sensors 206 may include, but are not limited to, a still camera, a video camera, an infrared camera, an ultraviolet camera, a sonic detector, a temperature sensor, a pressure sensor, a proximity sensor (e.g., a sonic proximity sensor, an infrared proximity sensor, etc.), and any combination thereof. The still camera, which may include an optional light source to illuminate an observed area, may be used to provide high resolution images of the observed area. The video camera, which may include an optional light source to illuminate the observed area, may be used to provide a visual inspection of the observed area in real time, slow motion, and/or time lapsed video. Other suitable cameras and/or video cameras may be used to detect one or more signals that may not be detected by the still camera or the video camera. For example, the infrared camera may be used to detect the heat signature of the observed area, which may be useful in detecting overheating in a mechanical component being observed. Additional sensors such as sonic detectors may be used to perform an ultrasonic measurement of an area, thereby allowing the detection of a material thickness (e.g., to indicate if degradation from an original thickness has occurred), subsurface cracks, voids, or other imperfections. Proximity sensors may allow the location of the inspection apparatus 106 relative to the structure 102 to be determined and recorded, thereby giving an indication as to the location of any degradation detected.

In an embodiment, the inspection apparatus comprises a plurality of sensors 206. Each of the sensors 206 may be used to inspect a different portion of the structure 102 and/or the access system 104. The sensors 206 may be used to inspect the access system 104 and the upper portion 107 of the structure 102. For example, a first sensor may be used to inspect, the access system 104 and a second sensor may be used to inspect the upper portion 107 of the structure 102, which may comprise a component such as a motor, generator, compressor, or any combination thereof.

The power source 208 may comprise any suitable source of electrical or mechanical power capable of operating the one or more sensors 206 and/or the motor 202. In an embodiment, a plurality of power sources 208 may be used with the inspection apparatus 106, with one or more power sources 208 coupled to the sensor 206 and one or more power sources 208 coupled to the motor 202. Suitable power sources 208 may include, but are not limited to, internal or external sources of power such as batteries (e.g., metal acid batteries, metal hydride batteries, lithium ion batteries, lithium polymer batteries, etc.), an engine, a generator, and any combination thereof. When an external power source 208 is used, one or more cables (e.g., connection 116 in FIGS. 1A and 1B) may be used to couple the inspection apparatus 106 to the external power source 208 and/or controller 108, which may be located at the base of the structure 102, at the top of the structure 102, or at any point in between the base and the top. In an embodiment, the access system 104 may comprise a portion of the power source 208. For example, the access system 104 may provide the ground reference for use with a single electrical conductor cable coupled to the inspection apparatus 106. In another embodiment, one or more portions of the access system 104 may comprise an electrical connection comprising both a ground reference and a voltage source, using for example powered rails or cables to which the inspection apparatus 106 is electrically coupled.

The inspection apparatus 106 may comprise a communication system 210 for sending and/or receiving signals such as control signals, sensor outputs, status indicators, etc. The communication system 210 may comprise wired and/or wireless communication pathways. For example, one or more communication cables (e.g., connection 116 in FIGS. 1A and 1B) may be used to couple the inspection apparatus 106 and a controller 108. In an embodiment, the communication system 210 may comprise one or more network connectivity devices such as modems, modem banks, Ethernet cards, universal serial bus (USB) interface cards, serial interfaces, token ring cards, fiber distributed data interface (FDDI) cards, wireless local area network (WLAN) cards, and other well-known network devices. These network connectivity devices may enable the inspection apparatus 106 to communicate with the Internet or one or more intranets. With such a network connection, it is contemplated that the inspection apparatus 106 or a processor operatively coupled to the inspection apparatus, might receive information from the network, or might output information to the network in the course of performing the inspection of the structure 102. Alternatively, a wireless communication device utilizing a wireless communication protocol such as WiFi, BlueTooth, code division multiple access (CDMA), global system for mobile communications (GSM), long-term evolution (LTE), worldwide interoperability for microwave access (WiMAX), and/or other air interface protocols may be used to couple the inspection apparatus 106 to one or more additional components (e.g., the optional controller 108). An antenna 214 or other wireless transmitter may be coupled to the inspection apparatus 106 for use in sending and/or receiving one or more communication signals. For example, the sensor outputs may be transmitted from the inspection apparatus 106 to a controller 108 to allow an operator to view the sensor output, make decisions based on the outputs, and possibly provide instructions back to the inspection apparatus 106 as needed.

The inspection apparatus 106 may comprise a memory 212 for storing one or more control programs and/or sensor outputs. The memory 212 may be comprised of RAM and/or one or more disk drives, solid state memory devices, and/or optical memory devices. The memory 212 may be used for non-volatile storage of data (e.g., the outputs of one or more sensors 206), and the memory 212 may be used to store programs operable to control and operate the inspection apparatus, the at least one sensor 206, the motor 202, and/or the communication system 210. The memory 212 may be referred to in some contexts as computer readable storage media and/or non-transitory computer readable media.

The system 100 may also comprise an optional controller 108. The controller 108 may contain a portion of the functionality and/or components associated with the inspection apparatus 106. The controller 108 may also be used as the user interface for operating the inspection apparatus 106, viewing the one or more sensor outputs, and/or interacting with stored sensor output. In order to communicate with the inspection apparatus 106, the controller 108 may comprise a communication system configured to exchange communication signals with the inspection apparatus 106. Further, the controller 108, rather than the inspection apparatus 106, may comprise the memory 212 for storing the sensor outputs, which may be received from the inspection apparatus 106 through a wired or wireless communication system. In an embodiment in which the communication system on the inspection apparatus includes a network connection, the controller 108 may be distributed across a site. For example, a network interface may be provided near the inspection apparatus 106 to send, receive, and/or exchange communications with the inspection apparatus 106, while the controller 108 may be located at a separate network accessible location. Further, the controller 108 may be located in a control room while the inspection apparatus 106 may be located at the structure 102 to be inspected, and the inspection apparatus 106 and the controller 108 may communicate through a local area network and/or a wide area network.

With reference to FIGS. 1A and 1B, the system 100 may allow for an inspection of a structure 102 using the inspection apparatus 106 as described herein. In an embodiment, a method for inspecting a structure 102 may comprise providing an inspection apparatus 106 as described herein. An access system 104 coupled to the structure 102 may then be inspected using the inspection apparatus 106. The access system 104 may be inspected from a first end to a second end, where the first end may be the lower end, and the second end may be the upper end. During the inspection process, the inspection apparatus 106 may store the output of a sensor, and/or the output of a sensor may be transmitted to a controller 108 that may record the sensor outputs. The inspection apparatus 106 may use any of the sensors described herein or any combination of the sensors described herein to inspect the access system 104.

Once the access system 104 has been inspected, the inspection apparatus 106 may be located at or near the upper end of the access system 104 as shown in FIG. 1B. The inspection apparatus 106 may then inspect a portion of the structure 102, which may comprise an upper portion 107 of the structure 102. The inspection apparatus 106 may remain coupled to the access system 104 during the inspection of the upper portion 107 of the structure 102. In an embodiment, the upper portion 107 of the structure 102 may comprise a piece of equipment such as a piece of industrial equipment. The inspection apparatus 106 may then inspect the piece of equipment using the same sensor(s), a different sensor(s), or some overlapping combination of sensor(s). For example, a first sensor may be used to inspect the access system 104 while a second sensor may be used to inspect the upper portion 107 of the structure 102, which may comprise the piece of equipment. The various sensor outputs may be recorded in a memory coupled with the inspection apparatus 106.

At the completion of the inspection, the inspection apparatus 106 may be conveyed downward along the access system 104. During the conveyance downward, the inspection apparatus 106 may further inspect the access system 104 and/or the structure 102 using the one or more sensors. Upon returning to the tower end of the access system 104, the inspection apparatus 106 may be retrieved from the structure 102. When the inspection apparatus 106 records the sensor outputs in an on-board memory, the inspection apparatus 106 may be coupled to a controller 108 or other device to retrieve and use the sensor outputs upon retrieval of the inspection apparatus 106. Based on the results of the inspection, one or more actions may be taken such as repairing the structure 102, repairing a piece of equipment associated with the structure 102, repairing the access system 104, repairing a portion of the access system 104, or scheduling another inspection. In general, the information obtained during the inspection may allow any defects in the access system 104 to be identified and repaired prior to allowing the access system 104 to be used in a repair of the structure 102.

In some embodiments, the order of the inspection may be reversed. Rather than inspecting the access system 104 with the inspection apparatus 106 during the ascent of the inspection apparatus 106 up the access system 104, the inspection apparatus 106 may first ascend the access system 104 to inspect the structure 102 or any portion thereof. Once the structure 102 has been inspected by the inspection apparatus 106 coupled to the access system 104, the inspection apparatus 106 may inspect the access system 104 during the descent of the inspection apparatus 106 down the access system 104. This and other variations are considered within the scope of the present disclosure.

In some embodiments, the use of the inspection apparatus 106 described herein may allow for an automated inspection of the access system 104 and/or the structure 102. For example, the inspection apparatus 106 may be coupled to the access system 104, left to perform the inspection, and later retrieved for an analysis of the sensor outputs, all of which may be performed without user intervention. The inspection apparatus 106 may also be configured to automatically identify one or more types of degradation associated with the access system 104 and/or the structure 102. This may allow an inspection apparatus 106 to remain coupled to the access system 104 and perform periodic (e.g., once a day, once a week, once a month, once a year, etc) or non-periodic (e.g., upon a user initiated command) inspections. The inspection apparatus 106 may then utilize the communication system to transmit a signal (e.g., an alarm, one or more sensor outputs, etc.) indicating the detection of a degradation in the access system 104 and/or the structure 102.

Figure 3:
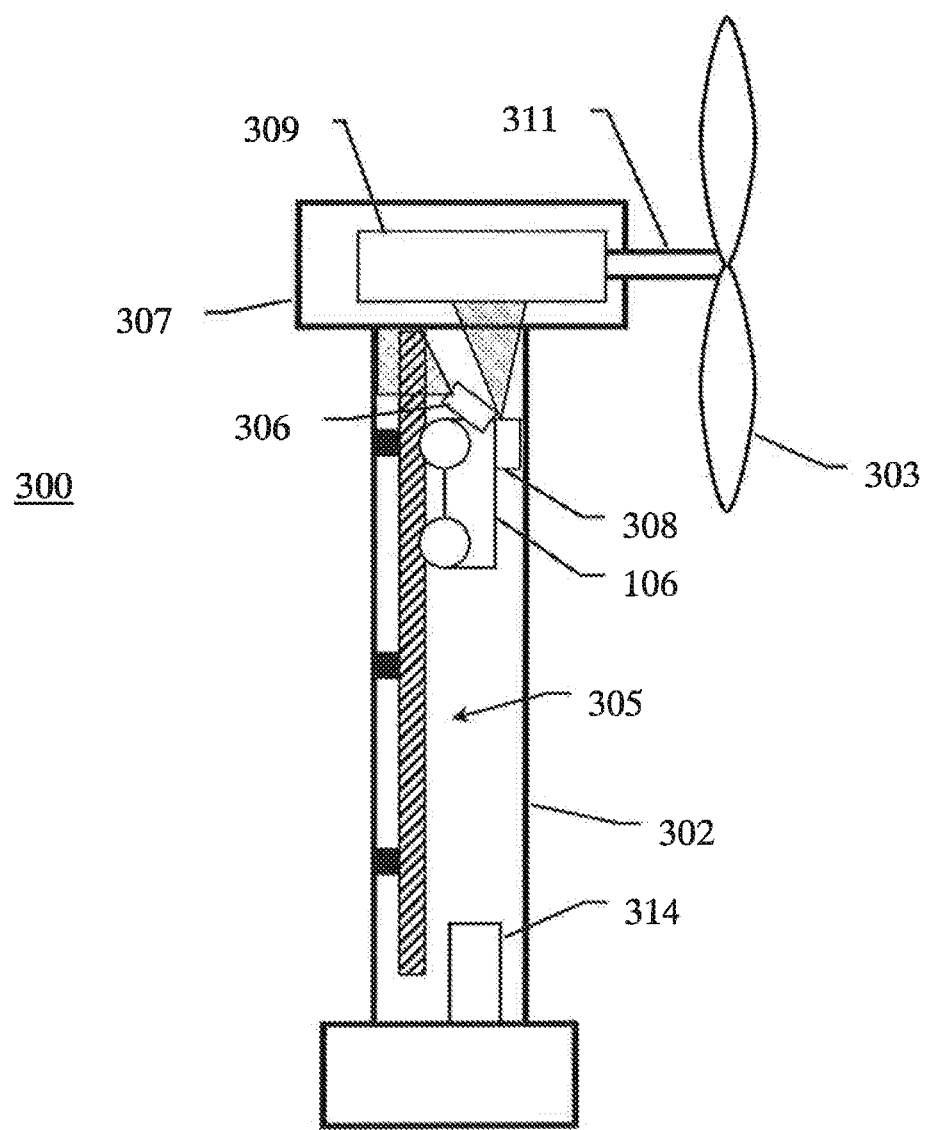
FIG. 3 schematically illustrates another inspection system according to an embodiment.

As a specific, non-limiting example of a method of inspecting a structure, the system can be described with reference to the inspection of a wind turbine tower 300. As shown in FIG. 3, wind turbine towers 300 may generally comprise a base support structure 302 supporting a turbine 303, generator 309, a rotor 311, and the associated equipment at the top of the base support structure 302. The access system 305 may comprise one or more ladders, rails or cables that may generally be disposed within the base support structure 302. An access panel 314 may allow access to the interior of the base support structure 302 to reach the access system 305.

Both the access system 305 and the equipment located at the upper portion 307 of the base support structure 302 may be inspected using an inspection apparatus 106 as described herein. Initially, the inspection apparatus 106 may be provided and engaged with the access system 305. The inspection apparatus 106 may be configured to ascend and descend along the access system 305. The appropriate drive mechanism may be engaged with the access system 305 to initially engage and position the inspection apparatus 106 on the access system 305. This process may be performed manually by disposing the inspection apparatus 106 in contact with the access system 305, or the inspection apparatus 106 may be configured to automatically engage and couple to the access system 305.

The inspection apparatus 106 may been inspect the access system 305. The inspection may comprise the use of a first sensor 306 to inspect the access system 305 as the inspection apparatus 106 traverses the access system 305 along its length. For example, the inspection apparatus 106 may use a video camera and an associated light source to provide a visual representation of the access system 305, its components, and the proximate structure during the inspection apparatus' ascent of the access system 305. The sensor output may be recorded in an on-board memory and/or the sensor output may be transmitted to a separate controller through a wired or wireless communication pathway.

Once the inspection apparatus 106 has inspected the access system 305 within the base support structure 302 of the wind turbine tower 300, the inspection apparatus 106 may be located at or near the top of the access system 305 within the base support structure 302 as illustrated in FIG. 3. The inspection apparatus 106 may then be used to inspect one or more of the pieces of equipment such as the generator 309, the portion of the rotor 311 within the tower, and any associated power transfer equipment. A second sensor 308 may be used to inspect the one or more pieces of equipment alone or in combination with the first sensor 306. For example, the inspection apparatus 106 may include an infrared camera to detect any overheating of any of the equipment components. The sensor 306 used in the inspection of the access system 305 may also be used. For example, both the infrared camera and the video camera may be used to inspect the equipment. This may provide both a visual inspection and an infrared inspection of the equipment located within the wind turbine tower 300. The inspection apparatus 106 may also inspect a portion of the wind turbine tower 300 at this time. After completing the inspection of the wind turbine tower 300 and/or the equipment, the inspection apparatus 106 may descend the access system 305. The inspection apparatus 106 may inspect the access system 305 and/or the base support structure 302 during the descent of the access system 305. Upon reaching the lower end or near the lower end of the access system 305, the inspection apparatus 106 may be retrieved from the access system 305. When the sensor output is stored in an on-board memory, the sensor output may be retrieved and reviewed to identify any potential degradation, equipment problems, or other conditions that may need attention or repair. Further, the inspection of both the access system 305 and the structure/equipment can be performed in a single trip.

Based on the results of the inspection, one or more actions may be taken such as repairing the wind turbine tower 300, repairing a piece of equipment associated with the wind turbine tower 300, repairing the access system 305, repairing a portion of the access system 305, or scheduling another inspection. As described above, the information obtained during the inspection may allow any defects in the access system 305 to be identified and repaired prior to allowing the access system 305 to be used in a repair of the structure or equipment located above an area of concern associated with the access system 305.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein. Other steps may be provided in the methods described herein, or steps may be eliminated, and other components may be added to, or removed from, the systems described herein. Other embodiments may be within the scope of the following claims.

What is claimed is:

1. A method of inspecting a structure comprising:
   providing an inspection apparatus comprising:
   a motor;
   a drive mechanism coupled to an access system, wherein the access system is coupled to a structure;
   a plurality of sensors; and
   a power source coupled to the motor and the plurality of sensors;
   inspecting the access system using a first sensor of the plurality of sensors as the inspection apparatus ascends the access system;
   inspecting a portion of the structure using a second sensor of the plurality of sensors;
   displaying a first output from the first sensor and a second output from the second sensor; and
   assessing whether the access system is safe;
   wherein the access system is configured to allow a person to access the structure at height.

2. The method of claim 1, wherein the drive mechanism comprises a suction cup, a pendulum motion device, a cam and crank mechanism, a magnetic attraction mechanism, or a gear and rail mechanism.

3. The method of claim 1, wherein at least one sensor of the plurality of sensors comprises a still camera, a video camera, an infrared camera, an ultraviolet camera, a sonic detector, a temperature sensor, a pressure sensor, or a proximity sensor.

4. The method of claim 1 further comprising repairing the access system prior to subsequent inspection of the structure by the person.

5. The method of claim 1, wherein the inspection apparatus further comprises a memory.

6. The method of claim 5, further comprising:
   storing the first output and the second output in the memory.

7. The method of claim 5, further comprising:
retrieving the first output and the second output from the memory; and
displaying the first output and the second output retrieved from the memory.

8. A method of inspecting a structure comprising:
providing an inspection apparatus;
engaging the inspection apparatus with an access system coupled to a structure;
inspecting the access system using the inspection apparatus; and
inspecting a portion of the structure using the inspection apparatus.

9. The method of claim 8, wherein the access system comprises a climbing system suitable for use by a human to access the structure at height, one or more connection elements, and one or more supporting elements.

10. The method of claim 9, wherein the climbing system comprises at least one structure selected from the group consisting of: a ladder, a rail, a cable, a stairway, and a foothold.

11. The method of claim 9, wherein the climbing system comprises one or more surface features.

12. The method of claim 8, wherein the inspection apparatus comprises a communication system.

13. The method of claim 12, wherein the communication system comprises a wired communication pathway, a wireless communication pathway, or both.

14. The method of claim 12, wherein the communication system comprises a network connectivity device.

15. The method of claim 12, wherein the communication system is coupled to a controller.

16. A method of inspecting a tower structure comprising:
providing an inspection apparatus configured to engage an access system coupled to a tower structure;
engaging the inspection apparatus with the access system;
inspecting the access system using a sensor coupled to the inspection apparatus as the inspection apparatus ascends the access system;
inspecting a piece of equipment disposed in an upper portion of the tower structure using the inspection apparatus; and
assessing whether the access system is safe:
wherein the access system is configured to allow a person to access the structure at height.

17. The method of claim 16, wherein a memory coupled to the inspection apparatus stores an output of the sensor during the inspection of the access system.

18. The method of claim 16, further comprising:
inspecting the access system, a portion of the tower structure, or both as the inspection apparatus descends the access system.

19. The method of claim 16, wherein the tower structure is a wind turbine tower.

20. The method of claim 19, wherein the piece of equipment comprises one or more components of a wind turbine selected from the group consisting of: a generator, a portion of a rotor, and an associated power transfer equipment component.

* * * * *